(12) United States Patent
Meeks et al.

(10) Patent No.: US 7,494,814 B2
(45) Date of Patent: Feb. 24, 2009

(54) APPARATUS AND METHOD FOR OBTAINING RAPID CREAMATOCRIT AND CALORIC CONTENT VALUES OF MILK

(75) Inventors: Jami E. Meeks, Sanford, FL (US); C. Diane Marshall, Cary, NC (US)

(73) Assignee: Separation Technology, Inc., Altamonte Springs, FL (US)

( * ) Notice: Subject to any disclaimer, the term of this patent is extended or adjusted under 35 U.S.C. 154(b) by 926 days.

(21) Appl. No.: 10/890,053

(22) Filed: Jul. 13, 2004

(65) Prior Publication Data

US 2006/0013733 A1    Jan. 19, 2006

(51) Int. Cl.
*G01N 33/06* (2006.01)
*G01N 33/04* (2006.01)
*G01N 9/30* (2006.01)

(52) U.S. Cl. .............................. 436/23; 422/72; 436/20; 436/22; 436/45; 436/71; 436/183; 494/7; 494/10

(58) Field of Classification Search ................. 422/72; 436/22–23, 45, 71, 183, 20; 494/7, 10, 16
See application file for complete search history.

(56) References Cited

U.S. PATENT DOCUMENTS

| 3,161,768 | A |   | 12/1964 | Goulden |
| 3,628,916 | A |   | 12/1971 | Werner |
| 3,684,450 | A | * | 8/1972  | Alder et al. .................. 436/45 |
| 3,746,511 | A |   | 7/1973  | Stookey et al. |
| 3,768,727 | A | * | 10/1973 | Proni ........................... 494/11 |
| 3,882,716 | A | * | 5/1975  | Beiman ...................... 73/61.66 |
| 3,972,625 | A |   | 8/1976  | Takahasi et al. |
| 4,212,948 | A | * | 7/1980  | Dorn ........................ 435/288.1 |
| 4,247,773 | A |   | 1/1981  | Nexo et al. |
| 4,738,655 | A |   | 4/1988  | Brimhall et al. |
| 4,887,458 | A |   | 12/1989 | Baker et al. |
| 4,927,545 | A | * | 5/1990  | Roginski ....................... 210/745 |
| 5,279,150 | A |   | 1/1994  | Katzer et al. |
| 5,354,254 | A |   | 10/1994 | Zabriskie et al. |
| 5,409,443 | A |   | 4/1995  | Zabriskie et al. |
| 6,548,304 | B2 |  | 4/2003  | Collins |

OTHER PUBLICATIONS

Fleet, I. R. et al, Journal of Physiology 1964, 175, 15-17.*
Ganguli, M. C. et al, Journal of Dairy Science 1969, 52, 126-127.*
Lucas, A. et al, British Medical Journal 1978, 1, 1018-1020.*
Lemons, J. A. et al, Pediatrics 1980, 66, 626-628.*
Collares, F. P. et al, Food Chemistry 1997, 60, 465-467.*
Goncalves, C. V. et al, Food Chemistry 1999, 64, 567-570.*
Wang, C. D. et al, Journal of Perinatology 1999, 19, 343-346.*
Meier, P. P et al, Journal of Perinatology 2002, 22, 646-649.*

(Continued)

*Primary Examiner*—Arlen Soderquist
(74) *Attorney, Agent, or Firm*—Andrus, Sceales, Starke & Sawall, LLP

(57) ABSTRACT

The invention relates to a centrifuge apparatus with a built-in sample tube reader and methods for rapidly obtaining measurements of creamatocrit, fat content and/or energy (caloric) content from low-volume fresh and frozen milk specimens.

7 Claims, 3 Drawing Sheets

OTHER PUBLICATIONS

Chan, M. M. et al, Journal of Pediatric Gastroenterology and Nutrition 2003, 36, 613-615.*

Verheul, F. E. A. M. et al, Journal of Clinical Chemistry and Clinical Biochemistry 1986, 24, 341-346.*

Entrez PubMed, National Library of Medicine, http://www.ncbi.mlm.nih.gov/entrez/query.fcgi?cmd=Retreive&db-pubmed&dopt=Abstr...; Creamatocrit: simple clinical technique for estimating fat concentration and energy value of human milk; Oct. 21, 2004, p. 1 of 1.

A comparison of lutein and zeaxanthin concentrations in formula and human milk samples from Northern Ireland mothers; VC Jewell, CBD Mayes, TRJ Tubman, CA Northrop-Clewes and DI Thurnham, European Journal of Clinical Nutrition, 2004, pp. 9097.

Quantitation of Human Immunodeficiency Virus Type 1 in Breast Milk; M.K. Ghosh et al, Journal of Clinical Microbiology, Jun. 2003, pp. 2465-2470.

Automation of the Rose Gottlieb method for fat determination in dairy products using an expert system; Alan R. Matheson and Patrick Otten, Americani Abortary; Mar. 1999, pp. 13-19.

"Creamatocrit, carbon content, and energy value of pooled banked human milk: implications for feeding preterm infants", L. Smith, J. Bickerton, G. Pilcher and S.W. D'Souza, *Early Human Development*, 11 (1985), pp. 75-80.

* cited by examiner

APPARATUS AND METHOD FOR OBTAINING RAPID CREAMATOCRIT AND CALORIC CONTENT VALUES OF MILK

FIELD OF THE INVENTION

The invention relates to a centrifuge apparatus with a built-in reader and methods for rapidly obtaining measurements of creamatocrit, fat content and/or energy (caloric) content of fresh and frozen milk specimens.

BACKGROUND OF THE INVENTION

Continuing efforts have been made to increase human neonatal survival rates with great progress towards improving the chances of survival for full-term and premature babies. Nutrition plays a key role in determining how well a newborn will thrive and develop. Nutritional information is, of course, provided with artificial formulas for infants. However, human breast milk is generally regarded as superior to formulas, giving infants a significant advantage with regards to growth and development, yet human breast milk is rarely analyzed with regards to fat content, which is directly related to energy content. Such information is critical to the care of premature infants and babies that fail to gain weight at a normal rate.

Many methods, as well as instruments employing such methods, have been developed for determining the fat content of milk. While some of the methods have enjoyed popularity in the dairy industry, none has gained widespread use or acceptance in clinical or health care settings. The Babcock method developed in the late 1800's became a standard procedure for determining milkfat content in the dairy industry. The procedure is somewhat hazardous, involving mixing a raw milk sample with concentrated sulfuric acid followed by heating and centrifugation of the mixture. Further, the Babcock method is not suitable for very small test sample volumes, for example, less than 100 microliters.

U.S. Pat. No. 3,161,768 to Goulden teaches a method of using infrared absorption, measured at the wavelength of absorption at the ester linkages (approximately 5.72 microns), for determining fat content of the disperse phase in an emulsion or suspension, such as milk. Such measurements are significantly affected by differences in diet and even genetic differences in cattle, but more reliable measurements are obtained when infrared absorption is measured at the carbon-hydrogen stretching wavelength (approximately 3.48 microns) as taught in U.S. Pat. No. 4,247,773 to Nexo et al. A disadvantage is that milk must be homogenized to reduce fat particle size in order to obtain meaningful data by such absorptiometric methods.

The International Dairy Federation published a standard procedure (IDF Standard 9C, 1987) for determining fat content of dried milk known as the Rose Gottlieb method. This gravimetric method is complicated, lengthy, and involves the use of solvents. Moreover, the milk sample must first be dried and the method is not suitable for small samples of milk less than 100 ml.

Other methods described for determining fat content include colorimetric methods, based upon a color reaction between milk fat and hydroxamic acid, and analysis of fat content by nuclear magnetic resonance (NMR). These procedures are complicated and require relatively expensive, specialized equipment.

In an attempt to develop a procedure with clinical applications, Lucas et al. described a simplified method for determining the fat and energy content of human milk based upon centrifugation of a small sample collected in a standard hematocrit capillary tube for fifteen minutes. See Lucas et al., Br. Med. J. 1:1018, 1978. The length of the cream layer is measured and calculated as a percentage of the total length of the milk column, for example, using a standard hematocrit-measuring card to determine the volume percentage of fat, referred to as a creamatocrit. Use of a hematocrit reader card requires the user to visually align several interfaces at once and then use the determined fat content to calculate estimated caloric content. Alternatively, calipers can be used to measure the cream column and the total length of the centrifuged milk specimen in the capillary tube, and the measurements obtained can be used to calculate the percentage of milkfat, with further calculations needed to determine estimated caloric content. In yet another method, micro-capillary readers can be used to mechanically determine fat content by manually aligning the capillary tube after centrifugation with an index mark, then aligning two rotating disks with the total length and the cream column; when a reading is determined, the user then must subtract the number from one hundred to obtain the percentage of milkfat and then perform further calculations to estimate caloric content.

Although the creamtocrit method represents a significant simplification in relation to other methods for determining milkfat content, it, too, has failed to secure broad acceptance in clinical settings. Further improvements directed towards shortening centrifugation time and to simplifying measurements and calculations of fat and energy content are needed in order for the creamatocrit technique to enjoy widespread use, particularly in clinical and public health care settings where the determination of fat and energy content of human milk is critical to neonatal and infant nutrition, as well as veterinary and research applications for non-human mammals.

SUMMARY OF THE INVENTION

The invention is an improvement to the existing creamatocrit technique comprising a centrifuge apparatus with a semi-automatic or fully automatic reader for entering data points determined from the centrifuged sample, as well as its use for rapid calculations of creamatocrit, estimated fat content, energy and/or caloric content.

BRIEF DESCRIPTION OF THE DRAWINGS

FIG. 4 shows a perspective view of an exemplary capillary tube containing a milk sample after centrifugation.

DETAILED DESCRIPTION OF THE INVENTION

In one embodiment, the invention comprises a centrifuge for separation of milkfat (cream) from the aqueous phase in small samples ($\leqq 100$ microliters) of milk, including, but not limited to, human breast milk. Prior to the present invention, creamatocrit procedures have been conducted using standard centrifuge devices with cavities for containing samples oriented either horizontally or at a fixed angle of about 45° with respect to the rotational axis. U.S. Pat. No. 4,738,655 to Brimhall et al. and U.S. Pat. No. 5,354,254 to Zabriskie et al., each incorporated herein in entirety, teach the use of a steeper angle, for example 70° to the horizontal plane (about 20° to the rotor axis), in order to significantly shorten the time required to sediment blood cells. The same principle is applied in the present invention with regards to centrifugation of milk samples with beneficial results in terms of decreasing centrifugation time needed for separation of the fat and aqueous phases. The time required for separating the cream and milk phases in the present invention is approximately no more than about three minutes.

Figure 1:
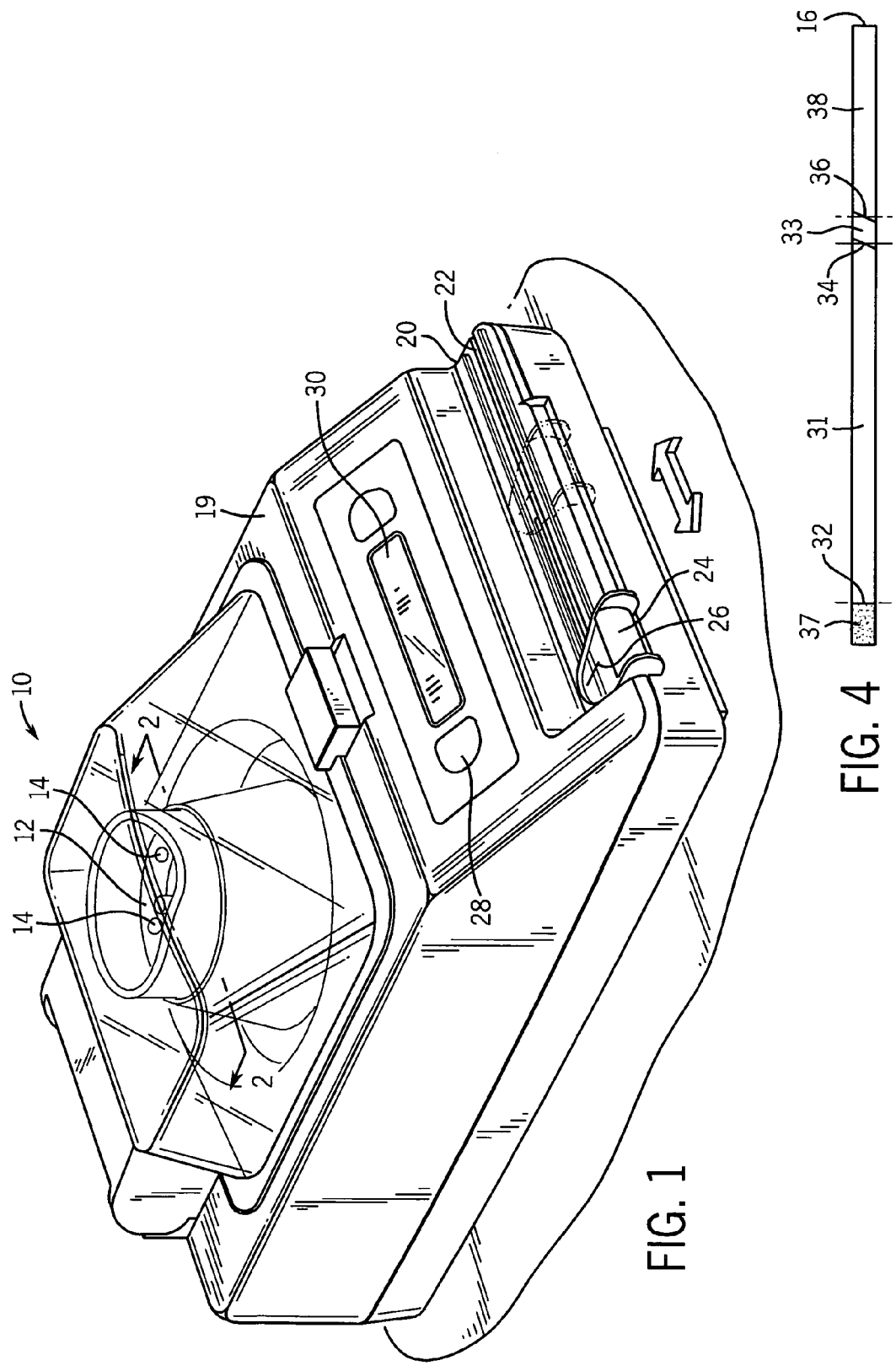
FIG. 1 shows a perspective view of one embodiment of the present invention, namely a centrifuge containing a sample tube reader.
Figure 2:
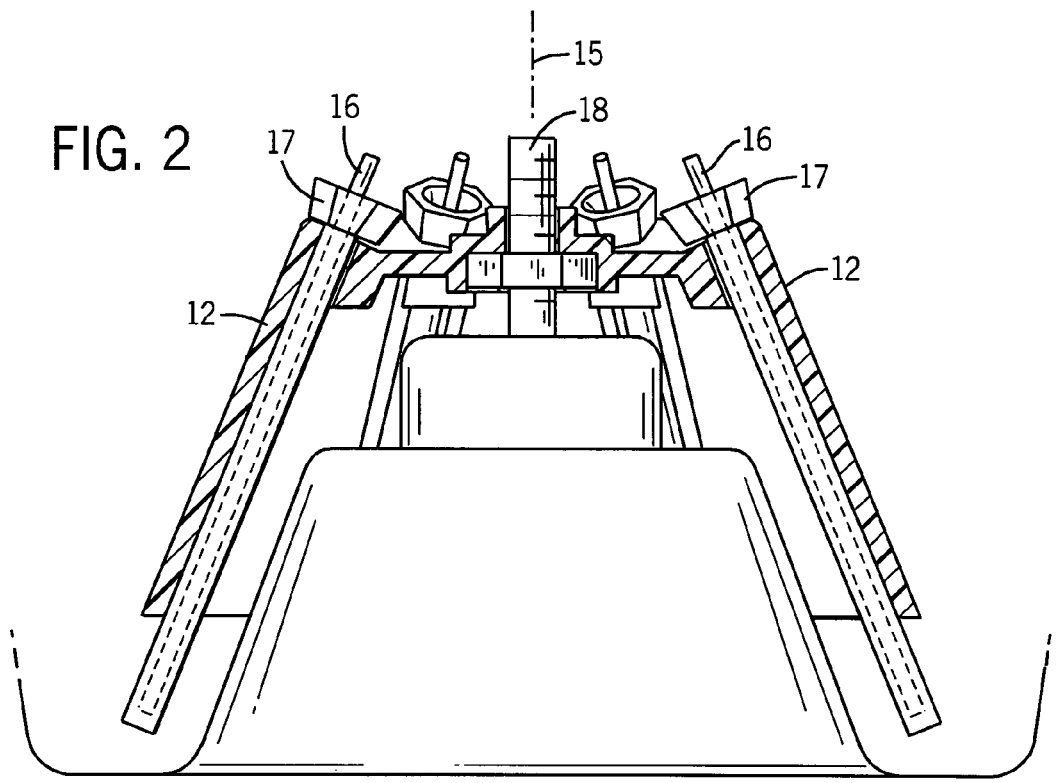
FIG. 2 shows a cross-sectional view of an embodiment of a rotor for a centrifuge of the present invention.
Figure 2A:
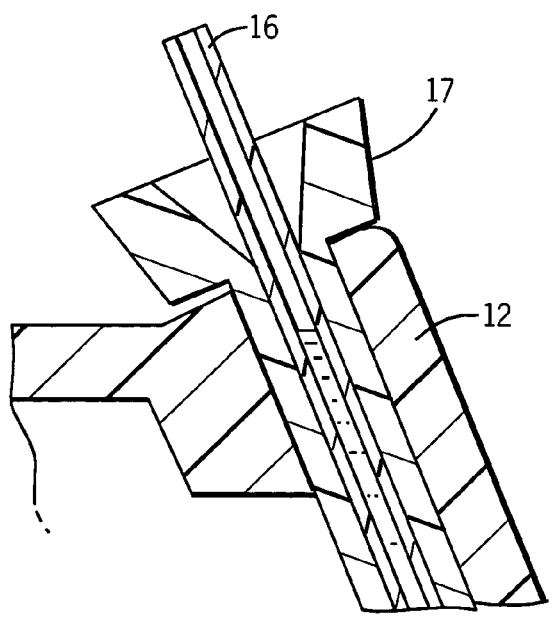
FIG. 2A shows an enlarged cross-sectional view through the capillary tube and tube holder within a cavity in the rotor.

FIG. 1 shows a perspective view of one embodiment of a centrifuge 10 with a fixed angle rotor 12 according to the present invention. The rotor 12 contains a plurality of circumferentially and evenly spaced cavities 14 for receiving standard non-heparinized hematocrit capillary tubes 16 containing milk samples. Preferably, the capillary tubes are placed within tube holders 17, as shown in FIGS. 2 and 2A, to contain milk samples in the event a capillary tube breaks during centrifugation. Such tube holders 17 prevent contamination of the centrifuge device 10 and operator by containing a potentially biohazardous specimen. A particularly useful type of tube holder 17 is disposable, made of transparent plastic and accepts capillary tubes with a maximum outer diameter of about 0.08 inches. Such tube holders are available from Separation Technology, Inc. (Altamonte Springs, Fla.). The cavities 14 are formed at a fixed angle to the rotor axis 15, indicated by the broken line in FIG. 2. A preferred angle is approximately 20° to the rotor axis 15, but can be within a range from about 15° to about 25° to the rotor axis 15.

The rotor 12 can be made from any number of materials known in the art that provide adequate corrosion resistance and strength, for example, aluminum, titanium, carbon fibers, or plastic polymers, such as acetal. Depending upon the material used, the rotor 12 can be machined, molded, stamped or otherwise manufactured by methods known in the art.

As further shown in FIG. 2, the rotor 12 connects to a shaft 18 driven by a motor (not shown), preferably one that operates on DC voltage, capable of spinning the rotor 12 at a maximum speed of about 5,500 to 7,000 r.p.m. and about 1,500 to 2,500 RCF. At a speed of about 6,000 r.p.m (about 1,750 RCF), a milk sample approximately 75 microliters in volume contained within a standard non-heparinized hematocrit capillary tube 16, is completely separated into cream and aqueous milk phases within approximately three minutes.

Preferably, a microprocessor is used to control the speed of the centrifuge 10, as is conventional in the art. For example, a Hall effect sensor can provide rotational speed input such that motor speed is continuously monitored and adjusted by the microprocessor. A particularly useful type of speed control is pulse width modulation (PWM) with a frequency of modulation at about 2,000 Hz. In a preferred embodiment, the motor is turned off if motor speed drops below a certain minimum speed, for example, about 5,670 r.p.m., and an optional error message indicating low speed is displayed. Additionally, the centrifuge can be designed so that the motor shuts down if the Hall effect sensor fails. Further, in a preferred embodiment, the motor is connected to a timer that fixes the spin time to a particular time span, for example 180 seconds, permitting the user to merely push a button or use some other form of initiation switch.

Additionally, the centrifuge 10 can include a battery pack (not shown), as known in the art, for operation as an alternative to other power sources. Rechargeable batteries, such as nickel metal hydride, are particularly suited for such use since they can charge while the centrifuge 10 is connected to an external power supply. If rechargeable batteries are used, the battery voltage is preferably monitored by the microprocessor to prevent overcharging.

Figure 3:
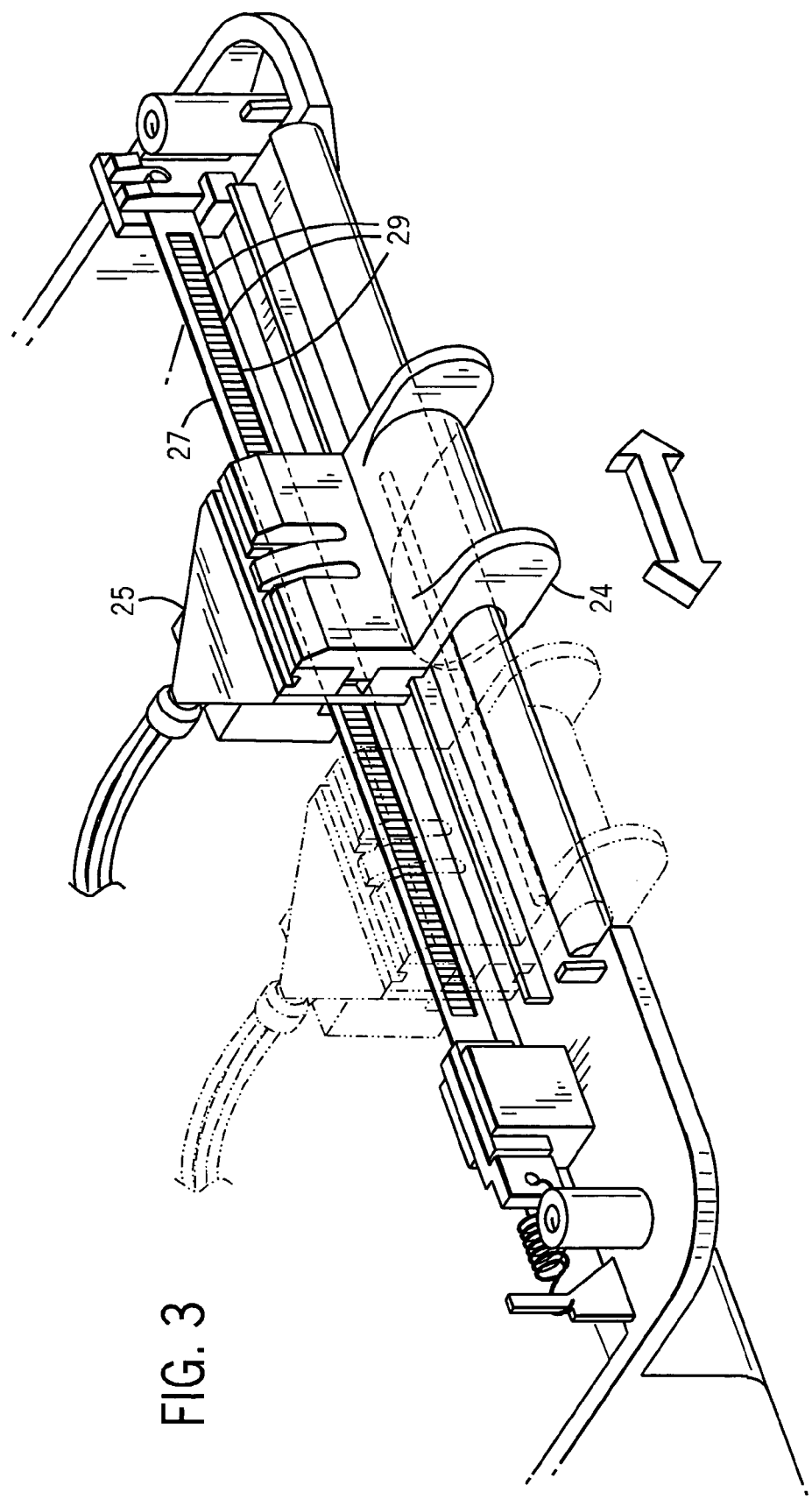
FIG. 3 shows a perspective view of an encoder and encoder strip with etched slots.

Referring again to the particular embodiment shown FIG. 1, the centrifuge housing 19 has an external platform 20 with a channel 22 for receiving a sample tube 16 after centrifugation, serving to facilitate the sample "reading" capabilities of the invention. A similar reader with semiautomatic capabilities is described in U.S. Pat. No. 4,887,458 to Baker et al., incorporated herein in entirety. The platform 20 and channel 22 are shown in a horizontal position in FIG. 1, but a vertical position is likewise suitable. In one embodiment, the user repositions a movable marker 24 with an alignment mark 26 to enter data points via a data entry button or switch 28. Referring to the embodiment shown in FIG. 3, the marker 24 is mechanically coupled to an encoder 25, for example an LED encoder, straddling an encoder strip 27. In a preferred embodiment, the encoder strip 27 is fabricated from a thin strip of electroformed nickel with etched vertical slots 29 approximately 0.003 inches wide. A spacing of approximately 0.0037 inches between the etched slots 29 provides a microprocessor with a resolution input of about 150 slots per inch. When the marker 24 is moved, for example by using a sliding motion as indicated by the arrow in FIG. 3, the signal is interrupted by the slots 29 providing data input to a microprocessor, enabling the microprocessor to monitor the exact position of the marker 24 during the tube reading process. Alternatively, the marker 24 can be mechanically linked to a rotary disk with slots designed to interrupt an LED or other emitter and sensor device. Likewise, instead of slots, the disk can have one or more magnets that rotate past a reed switch or Hall effect sensor.

The positional information produced by the movable marker 24 is in turn used by a microprocessor to determine the length of the cream column and the total length of the sample within the centrifuged capillary tube 16. A preferred microprocessor is a Motorola type 68HC11 microprocessor, but other suitable microprocessors are commercially available. A display window 30 located on the housing 19 displays results of calculations, as well as showing optional error messages and/or user prompts when appropriate. Several different types of displays are suitable including, but not limited to, diode array, ferroelectrics, plasma display panel, LED or preferably, a commercially available liquid crystal display (LCD).

In one embodiment, after a sample is centrifuged for approximately three minutes, two phases are observable, an aqueous phase 31 and a cream phase 33, and three interfaces are present as shown in FIG. 4: a first interface 32 between the sealant 37 and aqueous milk phase 31, a second interface 34 between the aqueous milk phase 31 and cream phase 33, and a third interface 36 between the cream phase 33 and air space 38 in the capillary tube 16. In the event a clear yellow fluid layer is present on top of the spun specimen (not shown), the yellow fluid layer is included as part of the cream layer 33. As an example of one method of using the device, the user moves the marker 24 so that the alignment mark 26 is collimated with the sealant/milk interface 32 and presses or otherwise activates the data entry switch 28 to input the first data point. The marker 24 is then moved until the alignment mark 26 is positioned in the approximate center of the diagonal milk/cream interface 34, and the data entry switch 28 is again activated to input the second data point. The marker 24 is then moved until the alignment mark 26 is approximately centered on the cream/air interface 36. The third data point is entered via the data entry switch 28.

The electronics in the reader are conventional and are programmed so that after entry of all three data points, the creamatocrit reading is automatically displayed. The creamatocrit value is calculated automatically by comparing electronically the distance between the milk/cream and cream/air interfaces (length of cream phase) with the distance between the sealant/milk and cream/air interfaces (total length of sample), wherein the ratio of the measurements is multiplied by 100. Fat content can optionally be calculated, electronically as known in the art, according to the formula provided in Lucas et al. wherein estimated fat grams/liter=3.968+(5.917× creamatocrit percentage). The result is displayed in the display window 30. Estimated energy content in kilocalories (kcal) per liter can be calculated as 385.422+(55.656× creamatocrit percentage). Alternatively, other formulas may be programmed as desired, such as Calories per ounce determined by dividing kcal/L by 33.8141.

In addition to the semi-automatic format described above, another embodiment is a centrifuge with a fully automatic reader wherein a sensor comprised of a radiation emitter, for example, infrared or visible light, or other measurable emitter, and a sensor for detecting the emissions is used to scan the length of the sample tube after centrifugation. The sensor and electronic interface to a micro-controller (not shown), and software automatically determines the interfaces 32, 34, 36 and displays the creamatocrit and/or other calculations.

While several embodiments have been described, the present invention may be embodied in other specific forms, as apparent to those of ordinary skill in the art, without departing from the spirit of the invention.

We claim:

1. A method of evaluating a sample of milk for at least one characteristic from the group consisting of: creamatocrit value, fat content, or energy (caloric) content, said method comprising:
   a. collecting a milk sample in a capillary tube;
   b. centrifuging the sample for about 3 minutes or less at about 6,000 to 7,000 rpm in a centrifuge device comprising a rotor mounted on an electric motor, said rotor including at least one cavity for containing said capillary tube, and said at least one cavity formed at an acute angle within a range from about 15° to about 25° to the axis of rotation of said rotor; and
   c. determining the characteristic using the centrifuged sample.

2. The method of claim 1 wherein the sample is unprocessed human breast milk.

3. The method of claim 1 wherein the sample is a thawed specimen of previously frozen human breast milk.

4. The method of claim 1 wherein the volume of said milk sample is less than or equal to approximately 100 microliters.

5. The method of claim 1 wherein the sample is unprocessed milk from a mammalian species.

6. The method of claim 1 wherein the sample is previously frozen milk from a mammalian species.

7. The method of claim 1 wherein the centrifuge further comprises a reader for said capillary tube, said reader comprising:
   a channel for containing said capillary tube after centrifugation;
   a movable marker coupled to an encoder;
   a microprocessor for calculating at least one characteristic;
   a data entry switch electronically connected to said movable marker for providing data entry into said microprocessor when an alignment marker on said movable marker is collimated with preselected positions within said capillary tube in the channel; and
   a display area on the centrifuge for displaying at least one characteristic calculated by said microprocessor from at least some of the data entered;
   and the method further comprises:
   placing the capillary tube with centrifuged sample within the channel;
   moving the marker to a position marking an interface between a sealant for said capillary tube and the milk sample and electronically entering a first set of positional data;
   repositioning the marker to a position marking an interface between an aqueous milk phase and a cream phase of the centrifuged milk sample with said capillary tube and electronically entering a second set of positional data;
   repositioning the marker to a position marking an interface between the cream phase and air space within said capillary tube and electronically entering a third set of positional data; and
   reading a result displayed, wherein the result is automatically calculated by the reader from one or more of said first set, second set, and third set of positional data.

* * * * *